(12) United States Patent
Franz et al.

(10) Patent No.: US 10,285,597 B2
(45) Date of Patent: May 14, 2019

(54) PROCESS AND DEVICE FOR MONITORING A PATIENT DURING ANESTHESIA AND FOR DETERMINING THE COMBINED EFFECT OF A PLURALITY OF ANESTHETICS

(75) Inventors: Frank Franz, Lübeck (DE); Maral Haar, Hamburg (DE); Jürgen Manigel, Scharbeutz (DE); Kai Kück, Hamburg (DE); Susanne Stahlkopf, Hamburg (DE); Marcel Voigt, Schönberg (DE); Thomas Bouillon, Basel (CH); Martin Luginbühl, Hinterkappeln (CH); Peter Schumacher, Kirchlindach (CH)

(73) Assignees: DRÄGERWERK AG & CO. KGAA, Lübeck (DE); INSELSPITAL BERN, DIREKTION LEHRE UND FORSCHUNG, Bern (CH)

( * ) Notice: Subject to any disclaimer, the term of this patent is extended or adjusted under 35 U.S.C. 154(b) by 2349 days.

(21) Appl. No.: 13/005,810

(22) Filed: Jan. 13, 2011

(65) Prior Publication Data
US 2011/0105914 A1 May 5, 2011

Related U.S. Application Data

(63) Continuation of application No. 12/136,315, filed on Jun. 10, 2008, now Pat. No. 7,878,982.

(30) Foreign Application Priority Data

Jun. 30, 2007 (DE) .......... 10 2007 030 505
Aug. 17, 2007 (DE) .......... 10 2007 038 975

(51) Int. Cl.
*A61B 5/00* (2006.01)
*A61B 5/024* (2006.01)
*A61B 5/083* (2006.01)
*A61M 16/01* (2006.01)
*A61M 16/10* (2006.01)
*A61B 5/0205* (2006.01)

(52) U.S. Cl.
CPC ............ *A61B 5/0205* (2013.01); *A61B 5/024* (2013.01); *A61B 5/0836* (2013.01); *A61B 5/4821* (2013.01); *A61M 16/01* (2013.01); *A61M 2016/1035* (2013.01); *A61M 2205/502* (2013.01); *A61M 2230/06* (2013.01); *A61M 2230/205* (2013.01); *A61M 2230/30* (2013.01); *A61M 2230/432* (2013.01)

(58) Field of Classification Search
CPC combination set(s) only.
See application file for complete search history.

(56) References Cited

U.S. PATENT DOCUMENTS 6,186,977 B1 * 2/2001 Andrews et al. ............... 604/67
2006/0081244 A1 * 4/2006 Bouillon et al. ......... 128/200.24

OTHER PUBLICATIONS

Syroid et al. ("Development and Evaluation of a Graphical Drug Display", Anesthesiology 2002; 96:565-74).*

* cited by examiner

Primary Examiner — Christian Jang
Assistant Examiner — Mitchell E Alter
(74) Attorney, Agent, or Firm — McGlew and Tuttle, P.C.

(57) ABSTRACT

A process is provided for monitoring a patient being anesthetized, as well as a process for determining a combined effect of different anesthetics used. Devices for carrying out the processes are also provided.

26 Claims, 4 Drawing Sheets

PROCESS AND DEVICE FOR MONITORING A PATIENT DURING ANESTHESIA AND FOR DETERMINING THE COMBINED EFFECT OF A PLURALITY OF ANESTHETICS

CROSS REFERENCE TO RELATED APPLICATIONS

This application is a continuation of application Ser. No. 12/136,315 filed Jun. 10, 2008, which claims the benefit of priority under 35 U.S.C. § 119 of German Patent Application DE 10 2007 030 505.4 filed Jun. 30, 2007, and DE 10 2007 038 975.4 filed Aug. 17, 2007 the entire contents of each of which are incorporated herein by reference.

FIELD OF THE INVENTION

The present invention pertains to a process for monitoring a patient being anesthetized by means of at least one anesthetic with the use of a monitoring device, which has a display means for displaying information concerning the anesthetic. The present invention pertains furthermore, to a device for monitoring a patient being anesthetized by means of at least one anesthetic with a display means for displaying information concerning the anesthetic. The present invention pertains, furthermore, to a process for determining a combined anesthetic effect for a patient being anesthetized by means of a combination of active ingredients and a device for determining a combined anesthetic effect for a patient being anesthetized by means of a combination of active ingredients.

BACKGROUND OF THE INVENTION

It shall be ensured for adequate anesthesia that the patient will not remember the procedure, the responses to painful stimuli are suppressed and circulation and respiration are maintained despite the highly potent drugs necessary for this, and the oxygen supply of the brain and other organs is thus guaranteed at any time. It shall be ensured for this that the drugs used for the anesthesia are present at a reasonable concentration at their sites of action, e.g., in the brain in the case of centrally acting anesthetics, such as sedatives or centrally acting analgesics, such as opiates, or at the motor end plates between motor nerves and skeletal muscles in the case of paralyzing drugs, e.g., muscle relaxants. The necessary concentration may differ depending on the situation, e.g., due to the surgical procedures being performed. For example, the pain stimulus elicited by a skin incision in the upper abdominal region may be markedly weaker than the pain stimulus caused by incisions for resecting a kidney.

If the need for anesthetic action changes in the course of, e.g., a surgery, an adequate anesthesia shall ensure that this need is met as quickly as possible.

However, adequate anesthesia is characterized at the same time by the anesthetic drugs not being dispensed at excessively high doses, in order to, among other things:

minimize adverse side effects of the drugs used for the anesthesia, such as a secondary weakening of the intensity of contraction of the heart muscle or respiratory depression; and prevent avoidably high concentrations of anesthetic active ingredients from accumulating in endogenous storage sites or compartments such as fatty tissue, which excessively delay the desired end of an anesthesia due to reflooding.

Achieving adequate anesthesia is especially challenging for an anesthesiologist, among other things, because the concentrations of anesthetic active ingredients in the blood or at the site of action and the anesthetic effects resulting therefrom, such as analgesia, sedation and paralysis, are unknown to the anesthesiologist or are known to the anesthesiologist to a greatly limited extent only. This is especially true of drugs that are administered intravenously (i.v.). The situation is further aggravated by the fact that more than one anesthetic drug is often administered, and that especially the analgesics (e.g., opiates) and sedatives (e.g., propofol) synergistically interact with each other. For example, the degree of increase in the effect of propofol following an increase in the concentration of propofol at the site of action depends on an opiate concentration that is likewise present at the site of action.

Technical solutions, which can facilitate the control of an adequate anesthesia for the anesthesiologist, are known from the state of the art:

a. The effect of muscle relaxants can be measured directly, even though only on selected skeletal muscles, and not always on skeletal muscles that are relevant for the particular procedure (e.g., the thumb muscle).

b. The concentration of volatile anesthetic drugs can be measured during expiration in the breathing gas. The end-expiratory concentration thus measured reflects the concentration in the lungs. However, it reflects the concentration in the blood plasma to a limited extent only, and that in other tissues or at the site of action to an even more limited extent only.

c. The monitoring of electrical voltages between certain sites on the scalp (EEG) makes it possible to infer the electrical activity in the brain. Devices are known, by means of which these voltage signals can be interpreted by means of very demanding processes of digital signal processing and aggregated into a standardized value, which is in a—not always close—relationship with the depth of sedation of the patient. One example of such a device is the BIS™ monitor from the firm of Aspect Medical.

d. Processes are known by means of which the concentration curves of anesthetic drugs can be determined and predicted on the basis of models based on the knowledge of the quantities of drugs introduced into the patient intravenously or via the lungs. These models have been determined based on measurements on a plurality of patients and permit a certain adaptation to the patients actually involved by stating the age, body weight, etc., of the patient to be actually treated. These processes fall in the area of pharmacokinetics.

e. Furthermore, processes are known by means of which the anesthetic effects of the drugs being used can be determined from the quantities of active ingredient administered. These effects are frequently represented as a probability that a patient responds to a given stimulus (e.g., a skin incision or being spoken to/shaken). These probabilities are based on statistical models, which have been determined on the basis of measurements on a plurality of patients. These models can also describe the mutual interaction of a plurality of anesthetic drugs. These processes fall in the area of pharmacodynamics.

f. Furthermore, processes for the graphic display of pharmacokinetically and pharmacodynamically determined concentration and effect curves are known. These include displays on the time axis (time-based display) as well as displays of opiate concentrations versus sedative concentrations (concentration-based display as is described in Patent DE 10 2004 050 717 B3 and corresponding US2006081244—U.S. patent application Ser. No. 11/250,026 of Oct. 13, 2005, which is hereby incorporated by reference).

Besides the adequate anesthesia, as it was described above, the anesthesiologist also has the task of monitoring and possibly securing bodily functions, which are limited or threatened based on side effects of the anesthetic drugs, based on therapeutic or surgical procedures, or based on a disease of the patient. These bodily functions include, e.g., the blood pressure, body temperature and respiration.

A number of possibilities of procedures, e.g., hemodynamically active drugs, volume replacement (e.g., physiological sodium chloride solution), heating or cooling techniques and respirators, are available to the anesthesiologist to perform these tasks. To make possible the adequate control of the use of these possibilities of procedure, various measurement methods, by means of which relevant physiological variables or surrogates thereof can be measured, are available to the anesthesiologist. These include, e.g., the end-expiratory $CO_2$ concentration measurement, invasive or non-invasive blood pressure measurement, heart rate measurement, etc.

SUMMARY OF THE INVENTION

Against this background, the basic object of the present invention is to provide a process for monitoring a patient being anesthetized, which enables the anesthesiologist to better care for a patient being anesthetized during an adequate anesthesia as discussed above and especially to dispense the anesthetics more adequately. In addition, a suitable device and an anesthesia device are to be provided.

According to one aspect of the invention, a process is provided for monitoring a patient being anesthetized by means of one or more anesthetic. The process comprises the step of providing a monitoring device having a display means for displaying information concerning the one or more anesthetic and displaying physiological states (heart rate, MAP, et $CO_2$) of the patient, which are variable during the anesthesia, by means of the display means.

Thus, the present invention provides a process for monitoring a patient being anesthetized with at least one anesthetic with the use of a monitoring device, which has a display means for displaying current or relevant information concerning the anesthetic. In addition, physiological states of the patient, which change in the course of the anesthesia, are displayed by means of the display means.

An anesthetic is defined within the framework of the present invention as any drug known as an anesthetic or an active ingredient on which it is based and also combinations thereof, regardless of whether it is a volatile drug or a drug administered intravenously (by an i.v.). The definition of an anesthetic in the sense of the present invention also includes any drug that does not fall within the class of the typical anesthetics but which is likewise to be taken into account in connection with the anesthesia by the anesthesiologist when carrying out the present invention. The latter drugs and/or active ingredients include especially sedatives. In particular, drugs that have relevant interactions with the anesthetics being used, which are popularly called as such, are also included among the anesthetics here.

The "patient" of the present invention may be a human being, but the present invention may also be used in animals being anesthetized.

The physiological states of the patient, which are likewise displayed on the display means, can be indicated by measured values of hemodynamic, respiratory or other parameters or surrogates thereof, which are suitable for estimating the patient's status and are relevant for the anesthesiologist. Depending on the type of the therapeutic or surgical procedure, different physiological states can be displayed for the anesthesiologist by means of the display means.

For example, the following measured values, which are variable over time, can be displayed for a general surgical procedure on an otherwise healthy patient, who is intubated and respirated: heart rate, mean arterial blood pressure, end-expiratory $CO_2$ partial pressure, as well as the BIS value (Bispectral Index Monitoring, BIS Index for short, an indicator of the "depth of anesthesia" measured on the basis of an EEG).

Depending on the therapeutic procedure and the patient's context (e.g., co-morbidities), parameters may be eliminated or additional parameters may be important. For example, the respiration rate, the $O_2$ saturation and the tidal volume may be additionally displayed in case of a therapeutic procedure during which the patient is breathing spontaneously. The ST segment of the ECG (electrocardiogram) being recorded simultaneously as well as the inspiratory oxygen concentration may be additionally displayed in another example, in case of a surgical procedure during which the oxygen supply of the myocardium is relevant because of a past disease of the coronary vessels of the heart.

It is possible according to the present invention, for the first time ever, to make available to the anesthesiologist the information necessary for optimally controlling the anesthesia in such an easily accessible manner that the anesthesiologist can control and monitor the anesthesia with improved safety and precision. Since the anesthesiologist can recognize, for the first time ever, an interaction between information on the anesthetic or anesthetics being used and information on the actions of the anesthetics on the patient, which actions also depend on the procedure and/or the anesthesia, the anesthesiologist can improve the instantaneously necessary dispensing of the anesthetics being used as well as the necessary depth of anesthesia.

The present invention makes possible, furthermore, a reduced cognitive work load for the anesthesiologist due to the combination of individual, combined as well as mutually relevant information in one display or a display device. This may lead to a less early onset of fatigue of the anesthesiologist, as well as to improved course of anesthesia and increased patient safety compared to the procedure known from the state of the art.

The combination of information that pertains to the anesthetics being used as well as information that pertains to the instantaneous physiological status of the patient in a combined display device makes it, moreover, possible to obtain clues on whether the active ingredient models, which are always based on patient population statistics and according to which concentrations are determined, are also true in the individual case and whether these can be brought into line with the individual patients actually being treated and whether these can be checked on the basis of this patient. Corrections may possibly have to be made in the controlling of the anesthesia on the basis of the recognized deviations of the patient's behavior from the hypothetical model behavior, which in turn makes it possible to improve the anesthesia.

The present invention has, furthermore, the object of providing a process by means of which a combined anesthetic effect of a combination of active ingredients on the patient being anesthetized can be determined. Another object of the present invention is to provide a device suitable herefor and to propose an anesthesia device.

This object is accomplished according to the present invention by a process for determining a combined anesthetic effect on a patient being anesthetized by means of a combination of active ingredients. The process comprises the step of determining the concentration of each active anesthetic ingredient at the site of action, combining the actions of all active ingredients, including combining the actions of all active ingredients within each class of active anesthetic ingredients used and determining a synergistic interaction between the active anesthetic ingredients used for the anesthesia.

The concentration of every active ingredient is determined here at the site of action. Knowledge of the actual action of the active ingredient administered on the patient is thus of particular interest according to the present invention, contrary to the knowledge of the concentration alone, at which the active ingredient is present in the blood. In cases in which it is not possible to determine the actual concentration of one or more active ingredients at the site of action by measurement, this concentration may be replaced with the second most accurate concentration that can be measured. The concentration of each drug at the site of action can be determined with pharmacokinetic and/or pharmacodynamic models.

The action of all active ingredients used is combined in the process according to the present invention, and each active ingredient can be taken into account individually here, or a cluster formation is performed at first, by means of which active ingredients of one class are combined. Combination can be defined according to the present invention, for example, as an addition of the efficacy or potency of the active ingredients if they act on the same type of receptor or receptors. However, if they act according to mutually different action mechanisms, the actions of the active ingredients being used are combined corresponding to the type of interaction of these active ingredients, for example, either additively, synergistically or antagonistically. The interaction is additive, for example, between opiates, and the corresponding concentrations of the opiates being used at the sites of action can be added up in a scaled manner based on the respective C50 or EC50 values (corresponding to a mean efficacy or potency).

The procedure described generally above in connection with the analgesics is followed in the case of the sedatives/hypnotics (or volatile anesthetics, intravenous anesthetics) used. Volatile hypnotics can be "added up," for example, by means of a scaling to the MAC value (minimal alveolar concentration) concerning their efficacy.

Furthermore, a synergistic interaction between a plurality of, i.e., at least two active ingredients used for anesthesia is determined in the process according to the present invention. This interaction can be described by means of models, as they were published, e.g., by Greco W. R., Bravo G., Parsons J. C. *The search for synergy: a critical review from a response surface perspective*. Pharmacol. Rev. 1995 June; 47(2): 331-385; Minto C. F., Schnider T. W., Short T. G., Gregg K. M., Gentilini A., Shafer S. L. *Response surface model for anesthetic drug interactions*. Anesthesiology, 2000 June; 92(6): 1603-1616; Bouillon T. W., Bruhn J., Radulescu L., Andresen C., Shafer T. J., Cohane C., Shafer S. L. *Pharmacodynamic interaction between propofol and remifentanil regarding hypnosis, tolerance of laryngoscopy, bispectral index, and electroencephalographic approximate entropy*. Anesthesiology 100 (6): 1353-1372, 2004; and Bouillon T. W., Schumacher P. M., Leibundgut D., Shafer S. L., Zbinden A. M. *A Novel Mechanistic Model Based on the MAC Reduction Paradigm Describes Hypnotic-Opioid Interaction for Suppression of Responses to Stimulation*. Anesthesiology 2004; 101: A503. The full related contents of the publications cited are part of the present disclosure by reference.

In case of interactions that are not (yet) known from the state of the art, it is possible to extrapolate over the mean efficacy or potency between the drugs of one type of drug each (i.e., analgesics, on the one hand, or sedatives/hypnotics, on the other hand).

In case of volatile anesthetics, this can be done, in turn, by means of the Minimum Alveolar Concentration (MAC—a measure of potency for anesthetics) values, and this can be done by means of the C50 or EC50 values in the case of opiates.

The action of all active ingredients can be combined and a combined potency N, which is obtained from the drug types scaled over the mean efficacy or potency and an interaction term, can be described by means of such interaction models as well as the knowledge of the respective concentrations of the active ingredients at the site of action and the combination of the action of all active ingredients. The combined potency N can be shown via an inverted sigmoid function to a range of, e.g., 0 to 100, or 0 to 10 or to a range scaled correspondingly differently (e.g., by means of simple multiplication by a factor or division by that factor). The combined potency N can therefore be stated, for example as NSRI (Noxious Stimulus Response Index):

$$NSRI = 100 * \left(1 - \frac{(N/N')^{sl}}{1+(N/N')^{sl}}\right) \quad (1)$$

This NSRI index corresponds to the probability of a reaction or response of the patient to a painful stimulus. By skillfully selecting N' and sl (see below), a favorable working range can be defined concerning, e.g., the tolerance of a painful stimulus or the wakability of the patient. NSRI equals 100 in case of an alert and non-anesthetized patient, and it has the value 0 in case of the deepest anesthesia, and the values 0 and 100 are to be considered to be purely exemplary. The possible range of values may also be between other values. The display is therefore not limited to a scale of 0 to 100. Other displays are possible as well. In particular, the value range of NSRI can be changed, e.g., by linear transformation. The NSRI can be stated as a dimensionless numerical value. Moreover, it can indicate a prospective trend over time. Its display is comparable in this embodiment to the display of parameters for indicating the depth of anesthesia, such as the BIS obtained by means of EEG. In particular, it can be displayed in a time-related manner, i.e., with reference to concrete points in time in the future.

A plurality of graphic comparison values for controlling the anesthesia and for the wakability of the patient, e.g., an NSRI, at which 50% of the patients would tolerate laryngoscopy, can be integrated in the display to support the anesthesiologist. These comparison values are based, e.g., on known population values.

To estimate the interaction, the NSRI may be plotted additionally for comparison for one drug, for example, the sedative/hypnotic only. N is calculated for this (according to the calculation instructions of the selected interaction model) as if no analgesic (e.g., an opiate) had been administered. The NSRI is now calculated, as before, by means of formula (1). An analgesic effect—consisting of the direct effect of the analgesics and the gain in action based on synergistic interaction with the sedatives/hypnotics—can be estimated from the difference between the reduced NSRI thus calculated and the combined NSRI (also taking into account the analgesics). However, as can be recognized by the person skilled in the art, calculation alone, e.g., of an analgesic component or of the component of other drugs used, such as the hypnotic or sedative or of an interaction term is also possible by means of the present invention and is also covered by same.

The following model is suitable for displaying the depth of sedation as a continuum of sedation up to the lack of response to noxious or disturbing stimuli on a time-based scale. The following hypothesis makes it possible to display a response probability of the patient and a cumulated action of the active ingredient on an integrated scale.

The standard interaction surface model can be expressed as:

$$P = \frac{N^g}{1+N^g} \quad (2)$$

in which
P is the probability of tolerating a certain stimulus;
N is the combination of the active ingredient concentrations, standardized by means of C50 values corresponding to them and corrected by the interaction effect;
and
g is a slope factor, which indicates the slope of the concentration-vs.-response curve.

The formula $$N = \frac{C_{hyp}}{C50_{hyp} * A_{out}} \quad (3)$$

in which $$A_{out} = A_{in} * \left(1 - \frac{C_{opi}}{C50_{opi} + C_{opi}}\right) \quad (4)$$

applies to the sequential response model.

$A_{out}$ indicates a stimulus intensity in case of effects due to administered opioids, and $A_{in}$ indicates the stimulus intensity in the absence of opioids ($A_{in}=1$ indicates the "calibrating stimulus intensity"); consequently, the model describes the damping of the stimulus by the opioid.

$C_{hyp}$ and $C_{opi}$ indicate the concentrations of the hypnotic and of the opioid or of the respective combinations thereof, and $C50_{xxx}$ the corresponding C50 or EC50 values corresponding to the mean efficacy or potency. N is therefore a dimensionless value, which indicates the combined "effective concentrations" and is obviously independent from the intensity of the stimulus ($A_{in}=1$). They may not appear to be particularly intuitive at first glance, but it should be borne in mind that the relative damping to a stimulus is fully independent from the stimulus intensity, and that the value N necessary for the tolerance of a stimulus is calculated with inclusion of the stimulus intensity (see below).

Plotting N over time yields the corresponding time curve. The ratio of the concentrations to the action(s) of these concentrations is displayed as follows: the action(s) or selected endpoints can be displayed as ranges of tolerance probabilities (50%-90%) over time on an "action" scale. This requires the calculation of the necessary action for given probabilities.

The general surface equation (Equation (2)) can be solved for N. This yields $$N = \left(\frac{P}{1-P}\right)^{1/g} \quad (5)$$

Formula $$A_{out} = A_{in}, \quad N = \frac{C_{hyp}}{C50_{hyp} * A_{in}} \quad (6a, 6b)$$

is obtained by substituting Equation (3) and simplification based on the absence of opioids.

An N' can be calculated only as a function of the stimulus intensity $A_{in}$, the desired tolerance probability P and the known slope factor g:

$$N' = \left(\frac{P}{1-P}\right)^{1/g} * A_{in} \quad (7)$$

Examples of a tolerance of shaking and loud shouting (TOSS) with an $A_{in}=1$ by definition and tolerance of laryngoscopy (TOL) $A_{in}=2.83$ (corresponding to the C50 ratio of propofol for the tolerance of laryngoscopy as well as tolerance of shaking and loud shouting according to Bouillon T. W., Schumacher P. M., Leibundgut D., Shafer S. L., Zbinden A. M., A. Novel: *Mechanistic Model Based on the MAC Reduction Paradigm Describes Hypnotic-Opioid Interaction for Suppression of Responses to Stimulation. Anesthesiology*, 2004; 101: A50.

The use of a slope factor g of 3.46—as is estimated by means of sequential interaction modeling of propofol and remifentanil (cf. literature reference above)—yields the values in N units in Table 1 below.

| Probabilities | [N units] |
|---|---|
| P50% TOSS | 1 |
| P90% TOSS | 1.89 |
| P50% TOL | 2.83 |
| P90% TOL | 5.34 |

Resealing of N—especially when high anesthetic concentrations are reached—and the necessary resealing of the axis designations associated herewith as well as the resealing of the calibration lines of the TOL and TOSS ranges can be advantageously avoided by means of a retransformation using a sigmoid function of the following form:

$$NSRI = 100 * \left(1 - \frac{(N/N')^{sl}}{1+(N/N')^{sl}}\right) \quad (8)$$

in which
N' is the specific N' value at which an NSRI of 50% is reached; and
sl is a slope factor for the transformation of N into NSRI.

In case of a definition as in Equation (8), the NSRI has the value of 100 (i.e., without the use of active ingredients), if it is calculated as an example over NSRI=100*(1−(N/2.83)$^{sl}$/(1+(N/2.83)$^{sl}$) in the conscious patient, and NSRI trends towards the value 0 during the deepest anesthesia (i.e., at high concentrations of active ingredients).

This above-described scaling to values between 0 and 100 has the added advantage that the anesthesiologist is usually experienced in the handling of indicators, whose values are between 0 and 100, with 0 representing the deepest anesthesia and 100 the conscious patient (e.g., BIS, entropy).

If, as in the above example, N'=2.83, a 50% NSRI would correspond to tolerance of laryngoscopy by 50% of the patients (see Table 1), which corresponds to a reasonable choice. The slope factor should be set such that a good working range is obtained for the anesthesia range as well as for the wake-up range. If sl=2.18, the 90% tolerance of laryngoscopy is shown on an NSRI of (exactly) 20, and the wake-up range (90% to 50% TOSS) is shown as an NSRI of about 70 to 90.

The following configuration is proposed for a conventional pharmacokinetic/pharmacodynamic display, which is used in clinical routine for carrying out the present invention:
1. Display of the NSRI over time with predictions for the future based on current drug dosages;
2. Display of the NSRI with hypnotic drugs (hypothesis that no opioids were administered and there is no interaction) in the display, combined as in the above item (same axes);
3. Display of the concentration of hypnotic active ingredients (blood/end tidal and site of action) on separate axes over time with predictions for the future;
4. Displays of the concentration of one or more opioids (blood and site of active ingredient) on different axes over time with predictions for the future;
5. Provision of the possibility of inserting markers, bars and/or lines for individualizing the display of the active ingredient; and
6. Display of a wake-up prediction (especially display of the foreseeable point in time of wake-up).

Furthermore, the possible combinations may be very helpful:
1. Display of the hemodynamic status over time (pulse rate, blood pressure);
2. Display of processed EEG parameters over time (e.g., BIS, entropy); and
3. Display of other parameters of the multidimensional patient status, which are relevant for the anesthesia, over time.

The processes according to the present invention may be implemented with the respective devices according to the invention as well as with an anesthesia device, which may be designed, e.g., as a respirator (also known as a ventilator). Since the above-described advantages can also be gained to the full extent with the devices according to the present invention, reference is expressly made here to the above discussion of these devices to avoid repetitions. Advantageous variants are also discussed herein as well.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

The present invention will be explained in more detail below on the basis of the attached drawings, identical reference numbers designating identical structures and/or components. In the drawings.

DESCRIPTION OF THE PREFERRED EMBODIMENTS

Figure 1:
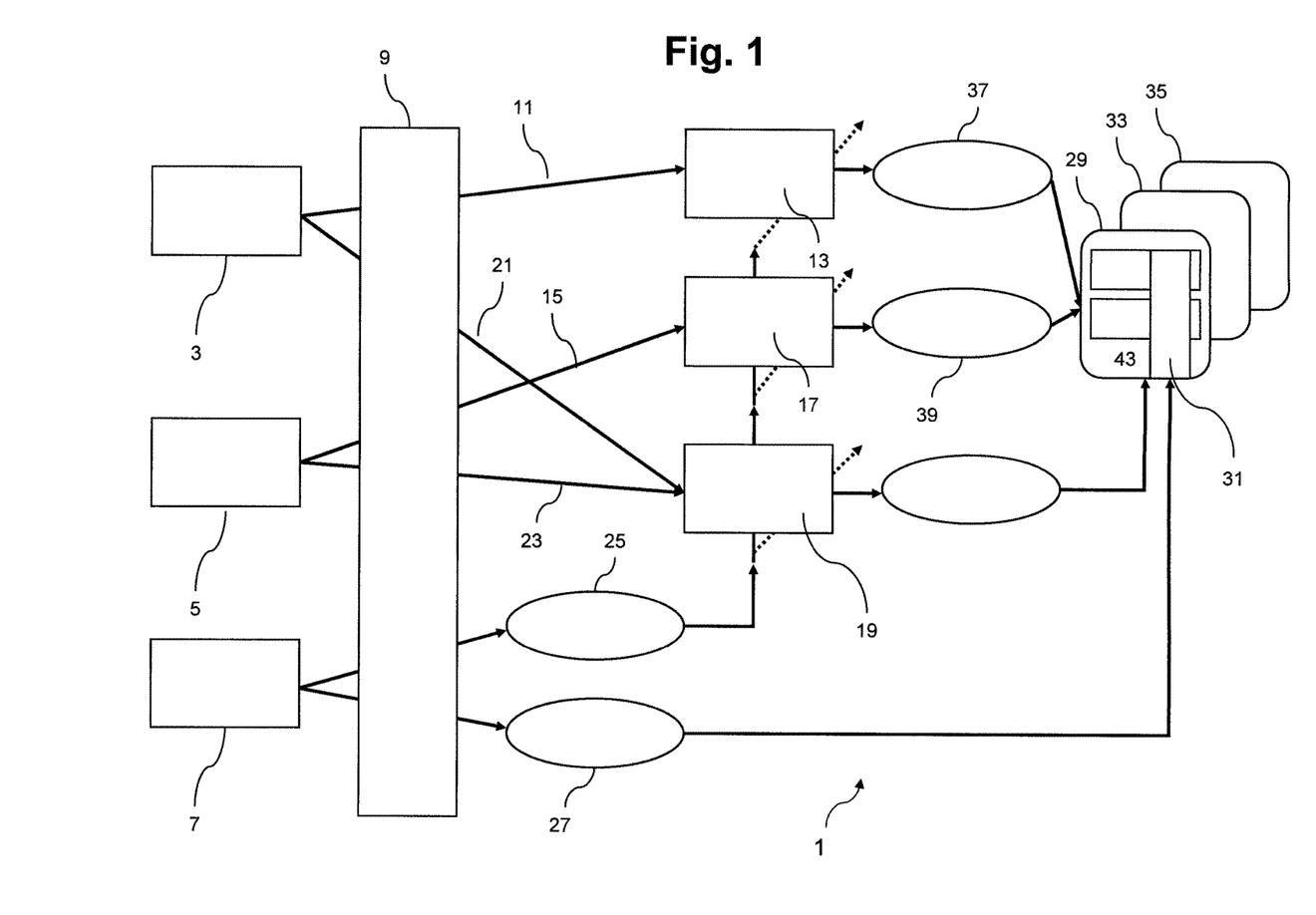
FIG. 1 is a schematic simplified view of a device according to the present invention with a display means.

Referring to the drawings in particular, FIG. 1 shows a schematic simplified view of a device 1 according to the present invention for monitoring a patient. This device 1 is designed, for example, as an anesthesia device, but the present invention is not limited to a device for monitoring an anesthesia. The device 1 has two i.v. pumps 3 and 5 for two anesthetics, wherein at least one of the pumps 3 and 5 for i.v. administration may also be designed as a means for administering a volatile anesthetic. Device 1 has, furthermore, an interface 7, by means of which data can be entered via a keyboard, a mouse or the like, not shown. Device 1 has, furthermore, an information management system 9, by means of which connection can be established between the anesthesia device, a hospital information system, a network and the like for providing data that are relevant in the particular case. Data from the i.v. pumps 3, 5 as well as from the interface 7 also enter this information management system 9. Information or data 11 on the dispensing of a first anesthetic by means of the i.v. pump 3 are sent in the device 1 according to the present invention shown in FIG. 1 to a first pharmacokinetic model 13. Information or data 15 on the dispensing of a second anesthetic administered by the i.v. pump 5 are sent to a second pharmacokinetic model 17. A pharmacodynamic model 19 receives information or data on the name, type or ID of the first anesthetic used, which is administered by the i.v. pump 3, as well as comparable data 23 on the second anesthetic administered by the i.v. pump 5. The two pharmacokinetic models 13 and 17 as well as the pharmacodynamic model 19 receive, furthermore, demographic data 25 on the patient being anesthetized. These demographic data 25 can be entered via the interface 7 or stored and are available for polling in the information management system 9. Furthermore, clinical observations 27 and other events can be passed on via the interface 7 and/or the information management system 9 for display in a display 29. For this, the display 29 has a means 31 for marking or indicating the onset of the event. A storage means 33 as well as a reproduction means 35 are attached to the display 29. Calculated or predicted data 37, 39 concerning the effect-time concentrations of the drugs administered can be sent by means of the first pharmacokinetic model 13 and the second pharmacokinetic model 17 (which may be complemented by additional models) to the display 29 for display in a concentration-based display 41 and/or in a time-based display 43. Data 45 sent from the pharmacokinetic model 19, which receives data from models 13 and 17—see the respective data stream indicated by broken line in FIG. 1—to the display 29, as they will be explained below in reference to FIG. 2.

Figure 2:
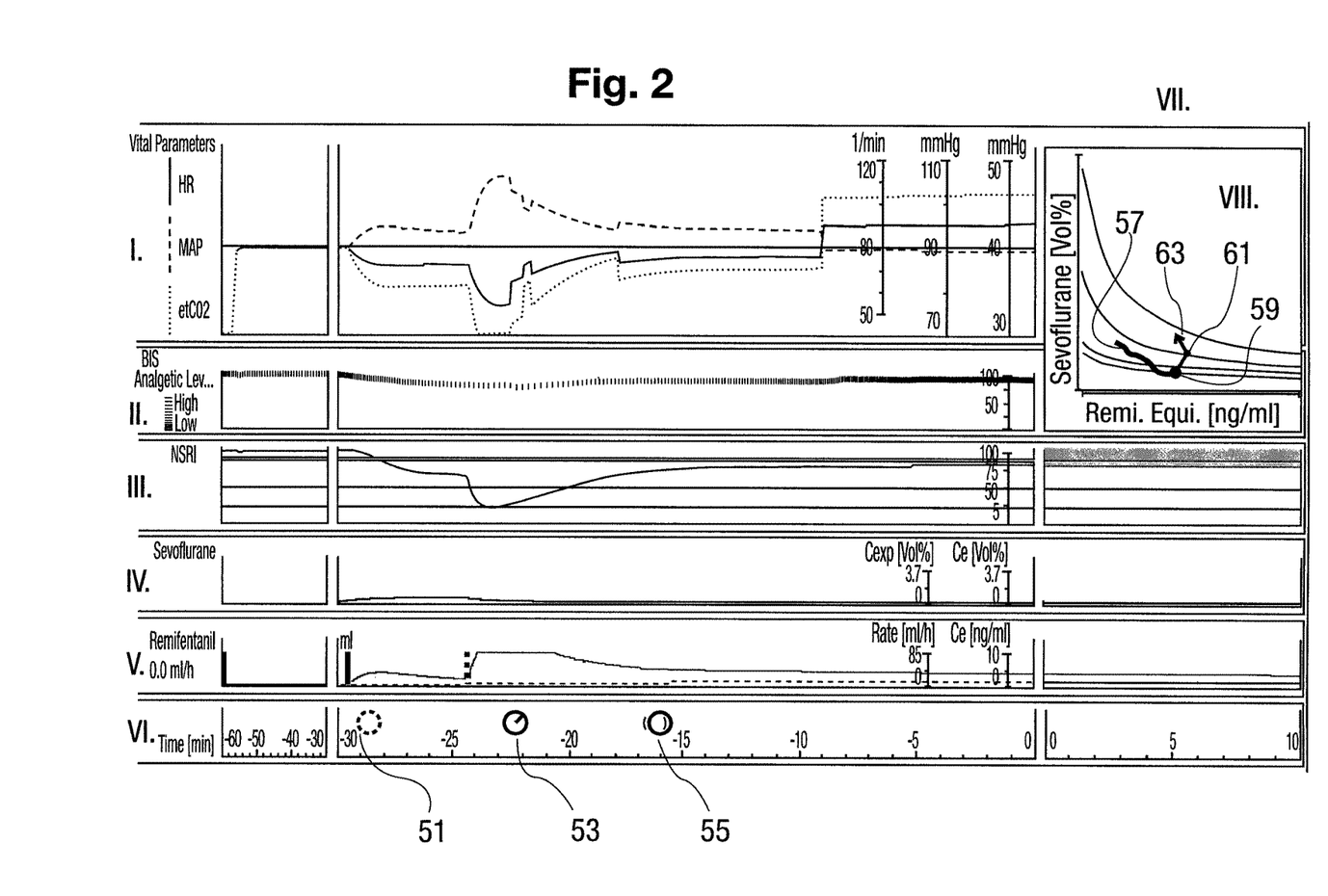
FIG. 2 is a view of the contents of a display device of an exemplary embodiment according to the present invention.

FIG. 2 shows a possible display according to the present invention on the display device 29 of a monitoring device according to the present invention. The pulse rate (HR, heart rate), the mean arterial pressure (MAP), as well as the expiratory $CO_2$ content ($CO_2$) are plotted over time (see section VI) in an upper section of the view in FIG. 2, which is designated by I.

The BIS is displayed as an indicator of the depth of anesthesia over time in section II. The index NSRI proposed according to the present invention is displayed as an another indicator of the depth of anesthesia on a scale from 0 to 100 in section III. The concentration of sevofluran over time is displayed in section IV, the concentration of remifentanil in section V, easily recognizable for the anesthesiologist at any time, the data in Ce[vol. %] corresponding to the concentration at the respective site of action.

The view in FIG. 2 shows in section VI other events marked by the reference numbers 51, 53 and 55, which may designate various events, such as skin incision, intubation, etc., during the anesthesia. The display of these events in the context with other pieces of information, such as time curve, dispensing of the drugs, etc., may provide the anesthesiologist with additional important information and relationships or explain such information or explain such information or relationships.

As can be seen on the right-hand side of the view in FIG. 2 under marking VII, displays directed towards the future can also be taken into account in the display according to the present invention. Thus, a concentration of sevofluran as well as remifentanil is shown in an isobole view in a concentration-based diagram VIII. Values that are in the past are marked in bold here and carry the reference number 57. The instantaneous concentration ratio of the two anesthetics (sevofluran and remifentanil) is marked by the dot with reference number 59. A prediction of what anesthetic concentrations and stimulus tolerances will be present in the near future (5 minutes or 10 minutes) is displayed by the curve 61 marked less bold as well as the trend indicated by means of arrow 63 in a clearly recognizable manner for the anesthesiologist. Concerning display VIII, reference is made, moreover, to the patent application with the German Patent Application number DE 10 2006 053 856.0-32 (which is hereby incorporated by reference in its entirety). The full content of this application related to this subject is thus part of the present disclosure by reference.

Figure 3:
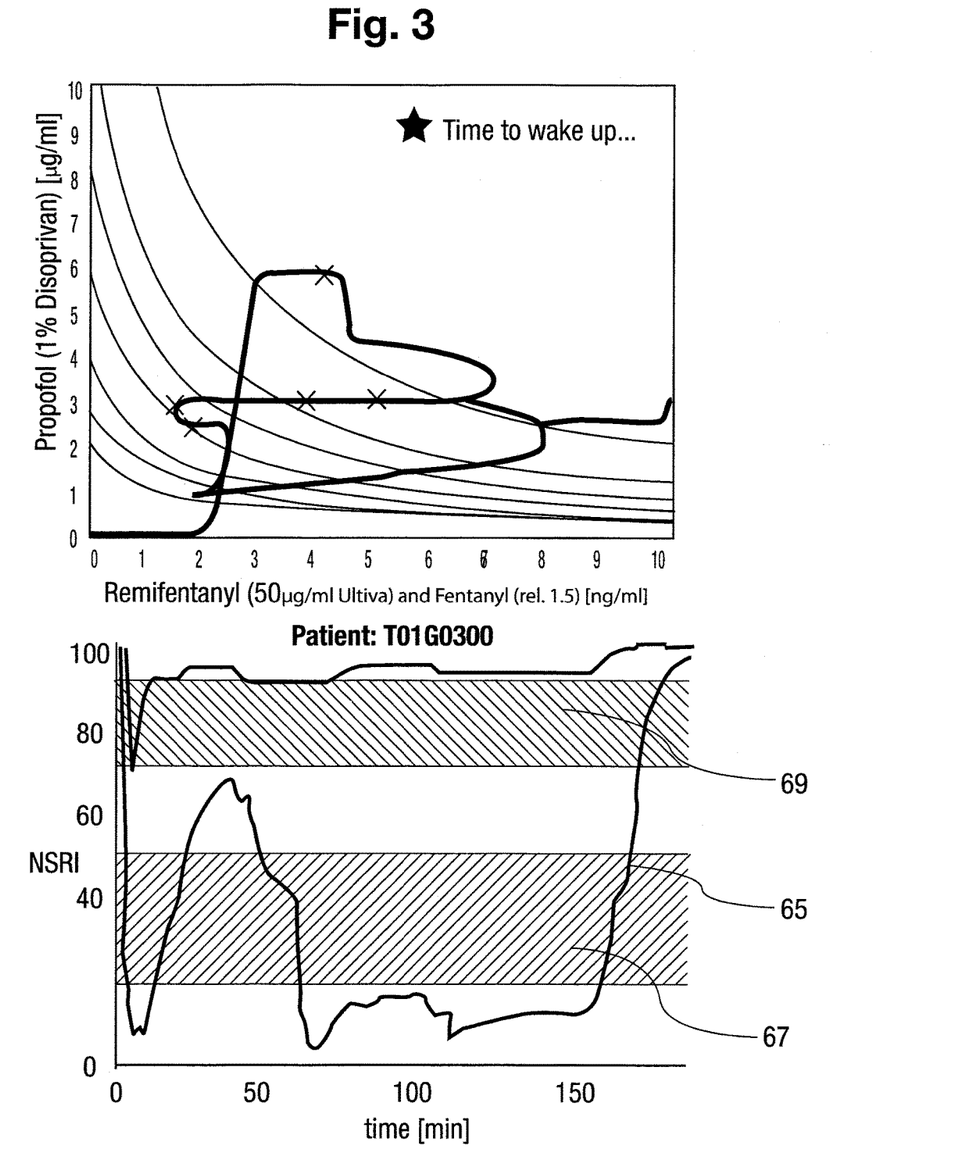
FIG. 3 is a view showing a form of display according to the present invention.

FIG. 3 shows two views of displays, which belong together and which have been generated during the anesthesia of the patient rendered anonymous under the designation "T01G0300." The upper view in FIG. 3 corresponds to a view that is the subject of the above-mentioned German Patent Application of this applicant bearing the number 10 2006 053 856.0-32. Reference is therefore made here for explanation to the application. The lower view in FIG. 3 shows the curve 65 of NSRI over the duration of the anesthesia.

Furthermore, the lower view shows two ranges 67 and 69 shown as shaded areas. Range 67 ranges here from an NSRI of 20 to an NSRI of 50. Range 69 ranges from an NSRI of 70 to an NSRI of 90. The range designated by 67 represents a range in which 90% to 50% of the patients tolerate laryngoscopy in this embodiment. Range 69 represents a range in which 50% of the patients do not respond to shaking and loud shouting.

Figure 4:
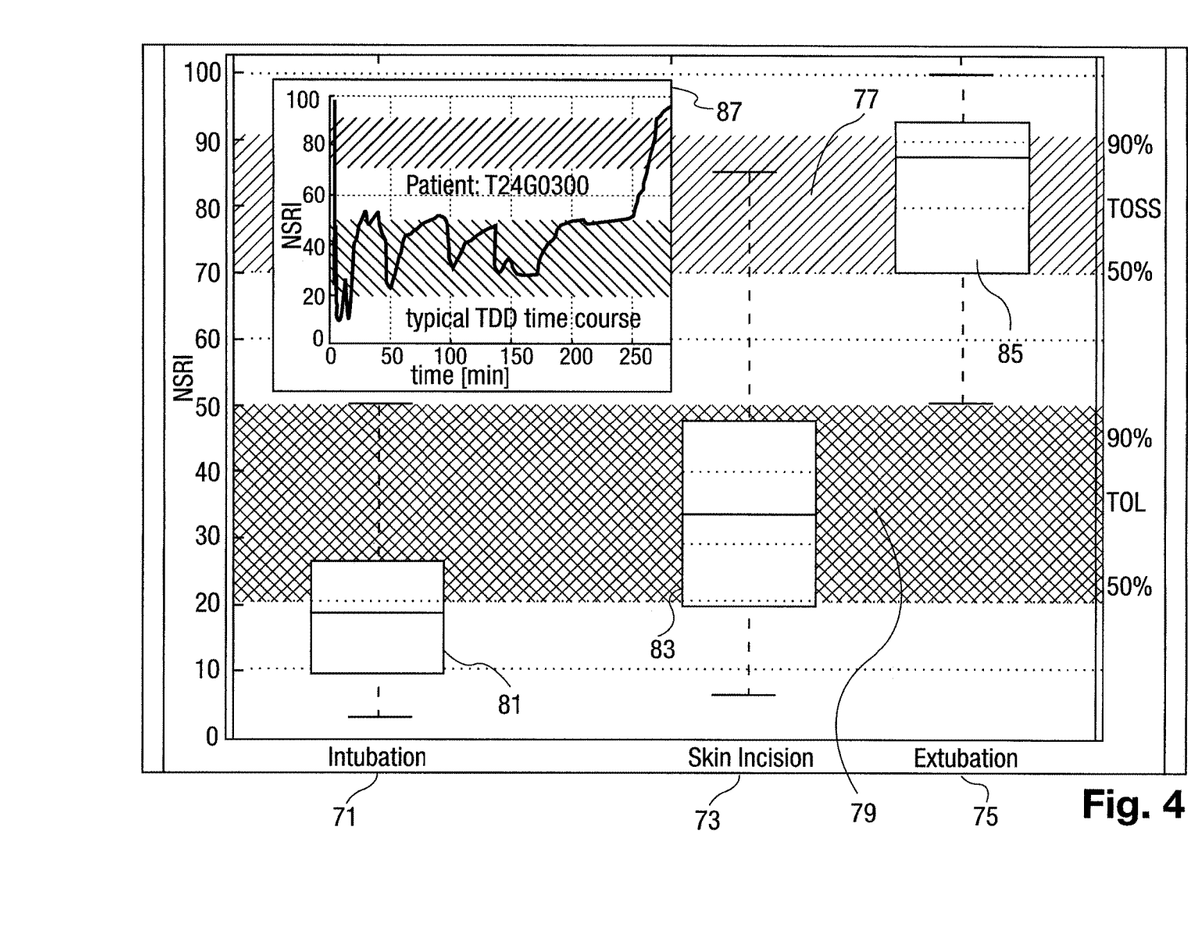
FIG. 4 is a view showing values of the NSRI according to the present invention for certain intraoperative events.

FIG. 4 shows a view according to the present invention of the NSRI for certain intraoperative events, namely, intubation 71, skin incision 73 and extubation 75 from the anesthesia of 35 patients, to whom propofol was administered together with remifentanil and fentanyl.

A first range 77 shown as a shaded area (which corresponds to range 69 in FIG. 3) is limited by the 90% TOSS as well as the 50% TOSS (Tolerance to Shaking and Shouting) and is prominently displayed (e.g., in color) on the display or display device for easier orientation for the anesthesiologist. This also applies to a second range 79, which is likewise shown as a shaded area (which corresponds to range 67 in FIG. 3), which is limited by the 90% and 50% TOL (tolerance of laryngoscopy).

The distributions of the NSRI for three events 71, 73 and 75 over the 35 patients are indicated by the reference numbers 81, 83 and 85.

Display 87 shows the NSRI curve 65 of a patient rendered anonymous with "T24G0300" over time.

Thus, the present invention provides a process for monitoring a patient being anesthetized as well as a process for determining a combined effect of different anesthetics used. It proposes, furthermore, devices for carrying out the process according to the present invention.

While specific embodiments of the invention have been shown and described in detail to illustrate the application of the principles of the invention, it will be understood that the invention may be embodied otherwise without departing from such principles.

What is claimed is:

1. An anesthetic process comprising the steps of:
administrating a plurality of active anesthetic ingredients to a patient undergoing a painful procedure;
determining a concentration of each of the active anesthetic ingredients at a site of action;
determining an action of each of the active anesthetic ingredients from the determined concentrations of each active anesthetic ingredient at the site of action;
determining an interaction relationship between each of the active anesthetic ingredients;
combining the actions of the plurality of active anesthetic ingredients according to the interaction relationship to obtain a combined potency of all the plurality of active anesthetic ingredients;
converting said combined potency to a Noxious Stimulus Response Index (NSRI), said NSRI being a one-dimensional parameter and having a full scale range with a first endpoint of said range indicating an alert and nonanesthetized patient, and with a second endpoint of said range indicating a deepest anesthesia;
displaying the NSRI to an operator controlling said administering of the plurality of active anesthetic ingredients.

2. An anesthetic process in accordance with claim 1, wherein:
the interaction relationship is calculated using a mathematical formula based on the individual potencies of each of the active anesthetic ingredients;
the NSRI is calculated using a mathematical formula based on the combined potency.

3. An anesthetic process in accordance with claim 1, further comprising:
grouping the active anesthetic ingredients into different classes based on action mechanisms;
combining the actions for each of the active anesthetic ingredients in each class to determine a class potency;
said determining of the interaction relationship is determined between the different classes of active anesthetic ingredients;
said combining of the actions includes combining the class potencies according to the interaction relationship to obtain the combined potency of all the plurality of active anesthetic ingredients.

4. An anesthetic process in accordance with claim 3, wherein:

5. An anesthetic process in accordance with claim 1, wherein:
said combined potency of the active anesthetic ingredients are based on a mean anesthetic efficacy of the active ingredients used.

6. An anesthetic process in accordance with claim 1, wherein:
said step of determining the interaction includes determining a synergistic interaction between the active anesthetic ingredients used for the anesthesia by means of extrapolation.

7. An anesthetic process in accordance with claim 1, wherein:
said combined potency of the anesthetic actions of the active ingredients administered is determined based on a mean anesthetic efficacy of the active ingredients used.

8. An anesthetic process in accordance with claim 1, further comprising the step of:
stating the combined potency as a value in a range from 0 to 100.

9. An anesthetic process in accordance with claim 1, wherein:
said combining of the actions of all active ingredients, includes combining the actions of all active ingredients within each class of active anesthetic ingredients used.

10. An anesthetic process in accordance with claim 9, further comprising the step of:
displaying said combined potency of a plurality of classes by means of a display means.

11. An anesthetic process in accordance with claim 10, further comprising:
displaying at least one comparison value for guiding the anesthesia and/or the wakability of the patient by means of said display means.

12. An anesthetic process in accordance with claim 1, further comprising the step of:
displaying all parameters that are variable over time over a time curve by means of a display means.

13. An anesthetic process in accordance with claim 1, further comprising the step of:
displaying a prediction of future values by means of a display means based on current drug dosages.

14. An anesthetic process in accordance with claim 1, further comprising the step of:
displaying a trend for the development of calculated values by means of a display means.

15. An anesthetic process in accordance with claim 1, further comprising the steps of:
providing a monitoring device having a display means for displaying information concerning the anesthetics; and
displaying physiological states of the patient, which are variable during the anesthesia including at least one of heart rate, mean arterial pressure, and expiratory $CO_2$ content, by means of a display means.

16. An anesthetic process in accordance with claim 1, further comprising the step of:
displaying pharmacokinetic and/or pharmacodynamic information concerning the anesthetic administered by means of a display means.

17. An anesthetic process in accordance with claim 1, further comprising the step of:
displaying a dispensing history of the one or more anesthetic.

18. An anesthetic process in accordance with claim 1, further comprising the step of:
adapting said administrating of the active anesthetic ingredients based on changes observed from said step displaying the NSRI in at least one parameter that is variable over time.

19. An anesthetic process in accordance with claim 1, further comprising the step of:
displaying information, which marks events of the anesthesia.

20. An anesthetic process in accordance with claim 1, further comprising the step of:
the operator adjusting said administrating of the plurality of active anesthetic ingredients to the patient depending upon said displaying of the combined potency.

21. An anesthetic process in accordance with claim 1, further comprising the step of:
providing one of said plurality of active anesthetic ingredients as an opioid;
providing another one of said plurality of active anesthetic ingredients as an non-opioid;
determining C50 values for each of said plurality of active anesthetic ingredients;
determining and standardizing the combined potency N of all the plurality of active anesthetic ingredients by means of C50 values corresponding to them.

22. An anesthetic process in accordance with claim 21, wherein:
said determining and standardizing of the combined potency N is performed using the formulas $$N = \frac{C_{hyp}}{C50_{hyp} * A_{out}}$$

$$A_{out} = A_{in} * \left(1 - \frac{C_{opi}}{C50_{opi} + C_{opi}}\right)$$

where: $A_{in}$ indicates the stimulus intensity in the absence of opioids;
$C_{hyp}$ indicates the concentrations of the non-opioid active anesthetic ingredient;
$C_{opi}$ indicates the concentrations of the opioid active anesthetic ingredient; and
$C50_{xxx}$ the corresponding C50 or EC50 values corresponding to the mean efficacy or potency.

23. An anesthetic process in accordance with claim 1, wherein:
said NSRI is calculated by $$NSRI = \left(1 - \frac{(N/N')^{sl}}{1 + (N/N')^{sl}}\right)$$

where:
N is the combined potency;
N' is a specific value at which an NSRI of 50% is reached; and
sl is a slope factor for the transformation of N into NSRI.

24. An anesthetic process comprising the steps of:
administrating a plurality of active anesthetic ingredients to a patient undergoing a painful procedure at a site of action, one of said plurality of active anesthetic ingredients being an opoid, another one of said plurality of active anesthetic ingredients being an non-opoid;

determining C50 values for each of said plurality of active anesthetic ingredients;

determining a concentration of each of the active anesthetic ingredients at the site of action using pharmacokinetic/pharmacodynamic models;

determining and standardizing a combined potency N of all the plurality of active anesthetic ingredients by means of C50 values corresponding to them;

converting said combined potency to a Noxious Stimulus Response Index (NSRI), said NSRI being a one-dimensional parameter and having a full scale range with a first endpoint of said range indicating an alert and non-anesthetized patient, and with a second endpoint of said range indicating a deepest anesthesia;

displaying the NSRI to an operator controlling said administering of the plurality of active anesthetic ingredients.

25. An anesthetic process in accordance with claim 24, wherein:

said determining and standardizing of the combined potency uses the formulas $$N = \frac{C_{hyp}}{C50_{hyp} * A_{out}}$$

$$A_{out} = A_{in} * \left(1 - \frac{C_{opi}}{C50_{opi} + C_{opi}}\right)$$

where: $A_{in}$ indicates the stimulus intensity in the absence of opioids;

$C_{hyp}$ indicates the concentrations of the non-opioid active anesthetic ingredient;

$C_{opi}$ indicates the concentrations of the opioid active anesthetic ingredient; and $C50_{xxx}$ the corresponding C50 or EC50 values corresponding to the mean efficacy or potency.

26. An anesthetic process comprising the steps of:

providing a plurality of pumps for administration of a plurality active anesthetic ingredients;

administrating a plurality of active anesthetic ingredients to a patient through the plurality of pumps;

providing an information management system for receiving data from the plurality of pumps about the administration of a plurality of anesthetics;

providing a plurality of pharmacokinetic models connected to the information management system;

determining a concentration of each of the active anesthetic ingredients at a site of action;

determining an action of each of the active anesthetic ingredients from the determined concentrations of each active anesthetic ingredient at the site of action;

determining an interaction relationship between each of the active anesthetic ingredients;

combining the actions of the plurality of active anesthetic ingredients according to the interaction relationship to obtain a combined potency of all the plurality of active anesthetic ingredients;

converting said combined potency to a Noxious Stimulus Response Index (NSRI), said NSRI being a one-dimensional parameter and having a full scale range with a first endpoint of said range indicating an alert and non-anesthetized patient, and with a second endpoint of said range indicating a deepest anesthesia;

providing a display means for displaying information concerning the anesthetic;

displaying the NSRI on the display means to an operator controlling said administering of the plurality of active anesthetic ingredients.

* * * * *